US00PP34818P2

(12) United States Plant Patent
Warren

(10) Patent No.: US PP34,818 P2
(45) Date of Patent: Dec. 13, 2022

(54) **JAPANESE *ZELKOVA* TREE NAMED 'JFS KW4ZS'**

(50) Latin Name: *Zelkova serrata*
Varietal Denomination: JFS KW4ZS

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 17/727,962

(22) Filed: Apr. 25, 2022

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

*Primary Examiner* — Susan McCormick Ewoldt
(74) *Attorney, Agent, or Firm* — Klarquist Sparkman, LLP

(57) ABSTRACT

A variety of *Zelkova serrata* with a combination of an upright branching vase shaped semi compact tree form with dark green foliage and orange to orange red fall color.

9 Drawing Sheets

Latin name of the genus and species of the plant claimed: *Zelkova serrata.*

Variety denomination: 'JFS KW4ZS'.

BACKGROUND OF THE INVENTION

In 2001, I began a program to create improved cultivars of Japanese *Zelkova, Zelkova serrata.* I searched through thousands of seedlings of *Zelkova serrata* growing in nursery rows in Canby, Oreg., Independence, Oreg., and Boring, Oreg. I walked along each row, looking for significant seedling variation that might hint at a unique and improved cultivar. From this search, I selected 50 seedling trees. The present tree was selected as an open pollinated seedling among seedlings of *Zelkova serrata* seedlings in Boring, Oreg. I marked and labeled this new tree, 'JFS KW4ZS', to be transplanted for further evaluation. It first caught my attention because it was more upright growing, with a sturdier trunk, better branching, dark green foliage, and a somewhat shorter internode length than typical seedlings of the species.

I dug this new tree during winter dormancy and transplanted it, along with the 49 other *Zelkova serrata* seedlings that were selected in this process, in a special evaluation row in the Boring, Oreg. nursery. During the summers of 2002 and 2003, I continued to evaluate this tree in comparison to the other special seedlings I had selected as well as typical *Zelkova serrata* seedlings. I became convinced that this tree had unique and improved characteristics that would be valuable as a cultivar in the nursery and landscape trade. In February of 2004, I transplanted 'JSF KW4ZS' and four other seedlings from this group of 50 into a special long term block where the spacing would allow it to grow to a larger and fuller form. The remaining 45 seedling trees were destroyed. Of the five trees planted in the long term block, one is 'JSF KW4ZS', one is 'JFS-KW1' U.S. Plant Pat. No. 20,996, and the other three were rejected and destroyed. Over the next several years, I continued to examine and evaluate my new tree in comparison to both seedlings and existing commercial cultivars of the species.

In August, 2011, I began a program to test asexual propagation of 'JFS KW4ZS' in small field plots in nursery rows in Canby, Oreg., by chip budding on *Zelkova serrata* seedling rootstock. I grew 'JSF KW4ZS' alongside existing cultivars of *Zelkova serrata* for comparison, namely 'JFS-KW1' (U.S. Plant Pat. No. 20,996), 'Green Vase' (U.S. Plant Pat. No. 5,080) and 'Musashino' (unpatented). I continued to direct that 'JSF KW4ZS' be chip budded in these small test plots in the Canby, Oreg. nursery, each year through 2017. A total of 93 test trees were produced in these plots. All of the test propagated nursery trees were destroyed after evaluation, except for 20 which I kept for stock increase. Evaluation of these asexually propagated trees demonstrates the valuable and unique characteristics of 'JFS KW4ZS' were firmly fixed in each successive generation.

BRIEF SUMMARY OF THE INVENTION

This new cultivar possesses a unique combination of characteristics that have proven firmly fixed in asexually propagated progeny and that comprise a combination of green foliage, and a more compact growth habit with a symmetrical upright branch structure.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
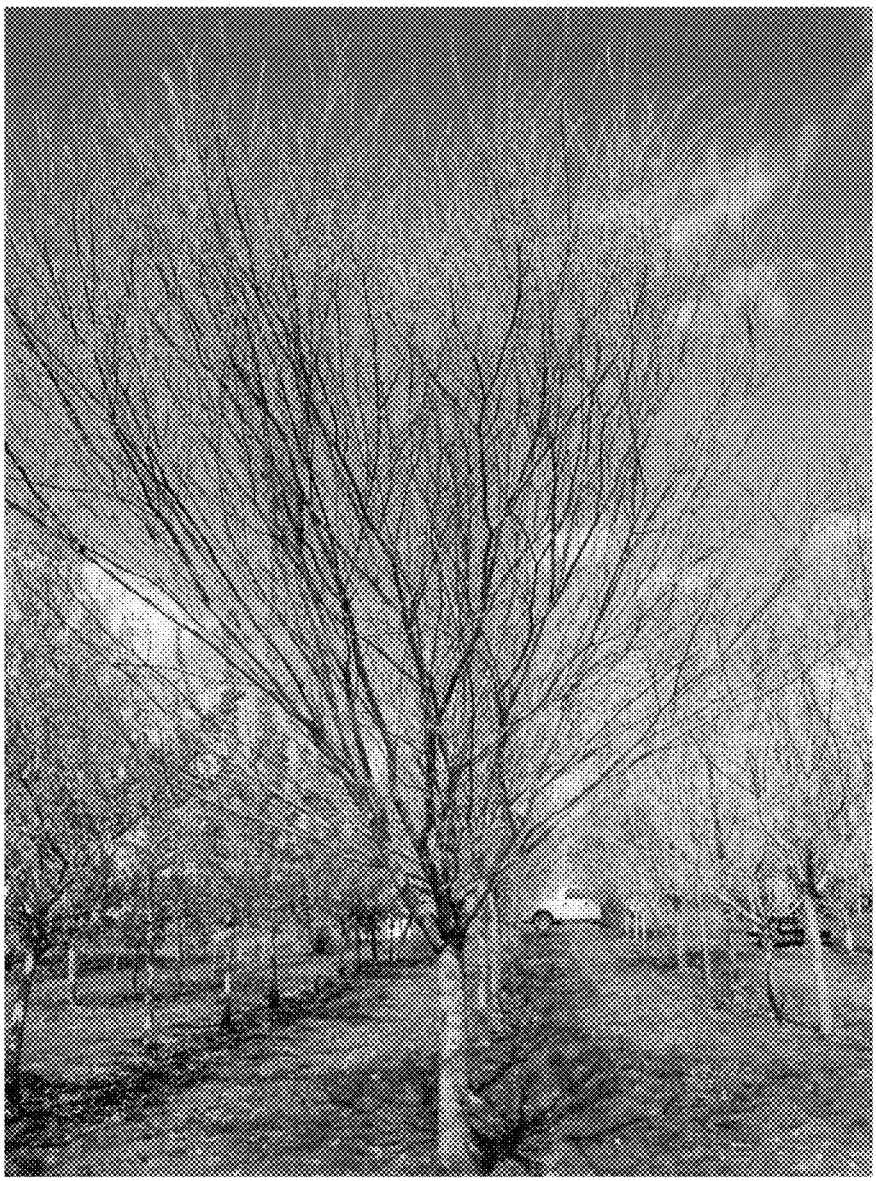
FIG. 1: Shows the branch structure of the tree at 10 years of age just before bud break.
Figure 2:
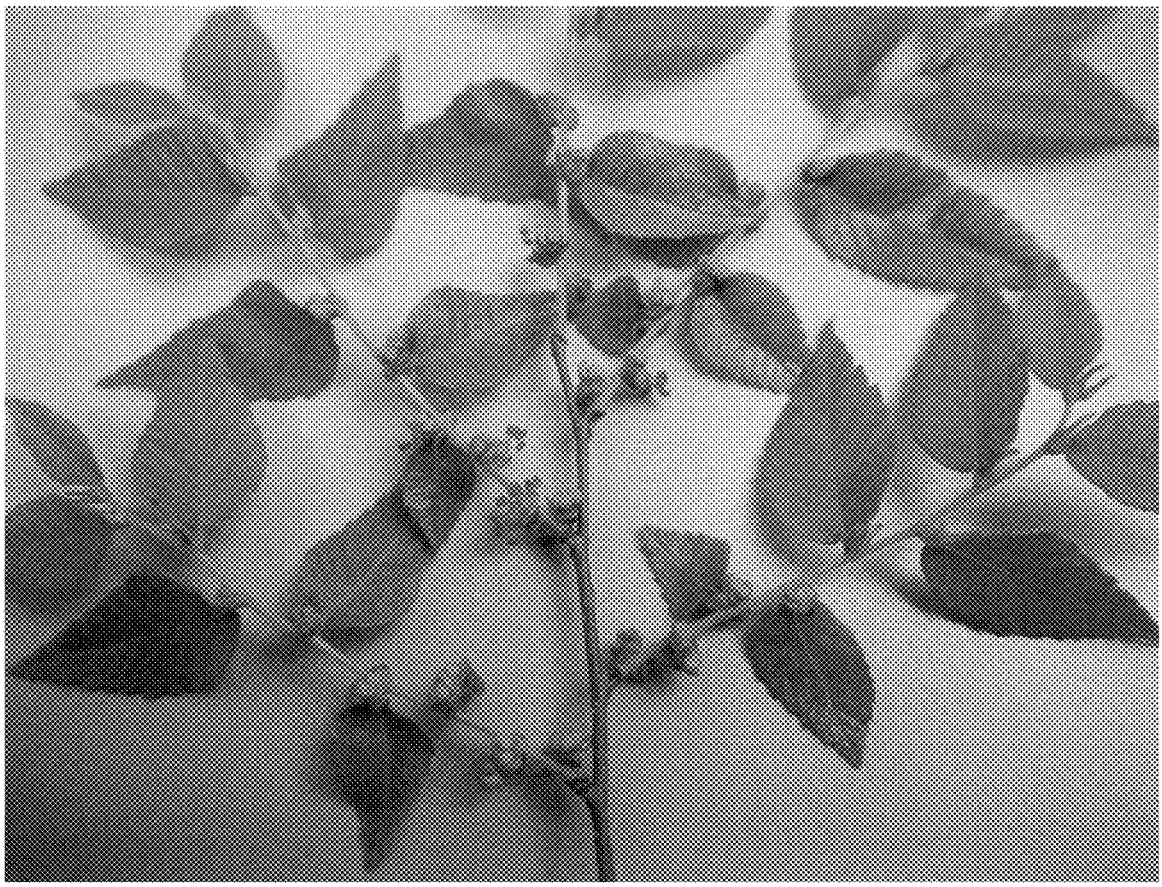
FIG. 2: Shows new foliage and staminate flowers on a display board.
Figure 3:
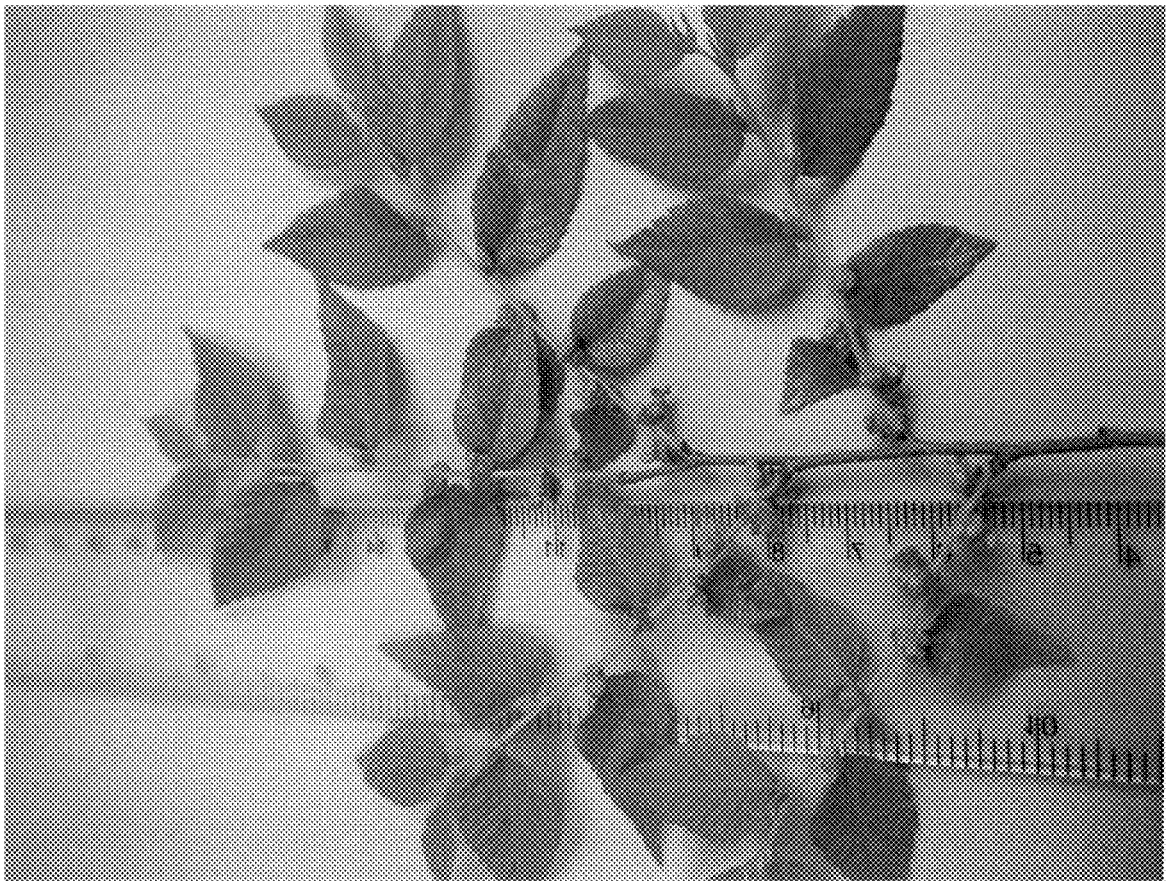
FIG. 3: Shows new foliage, staminate and pistillate flowers on a display board with scale.
Figure 4:
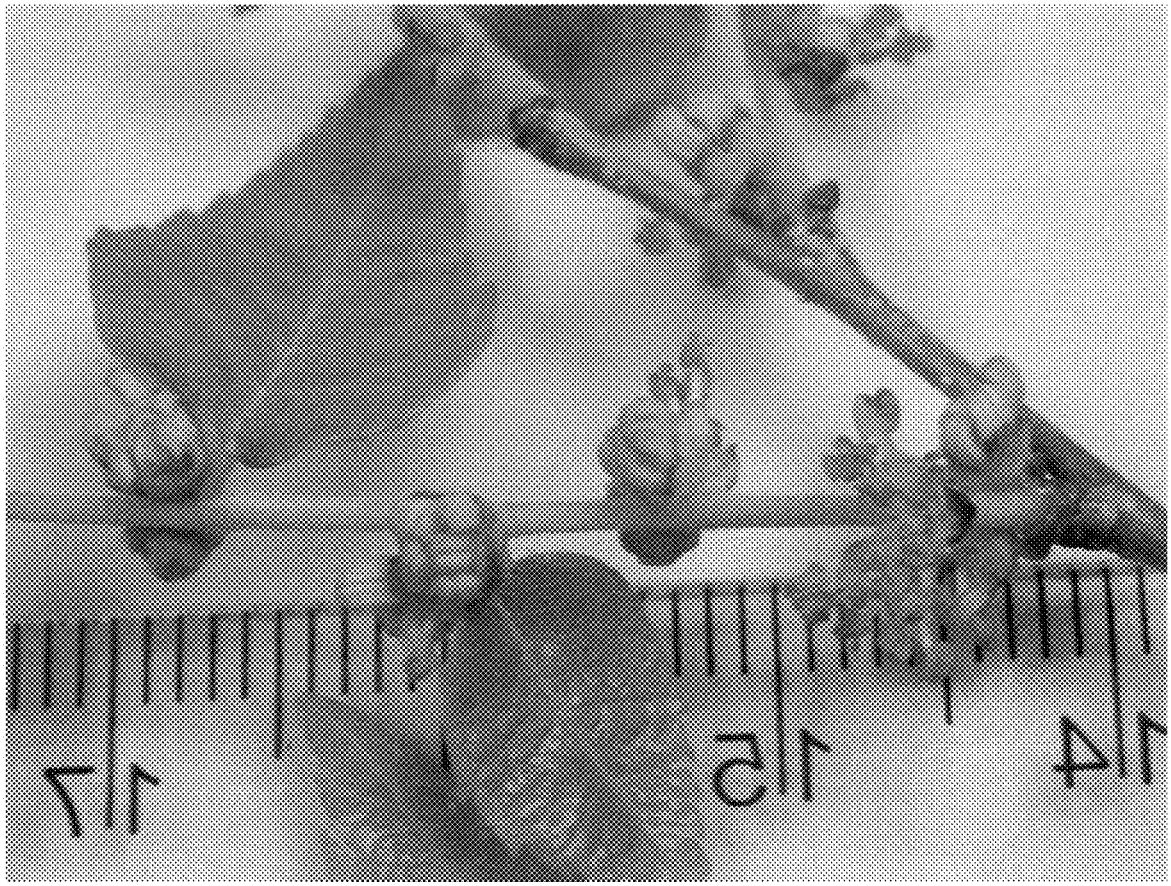
FIG. 4: Shows a close up of staminate flowers on a display board with scale.
Figure 5:
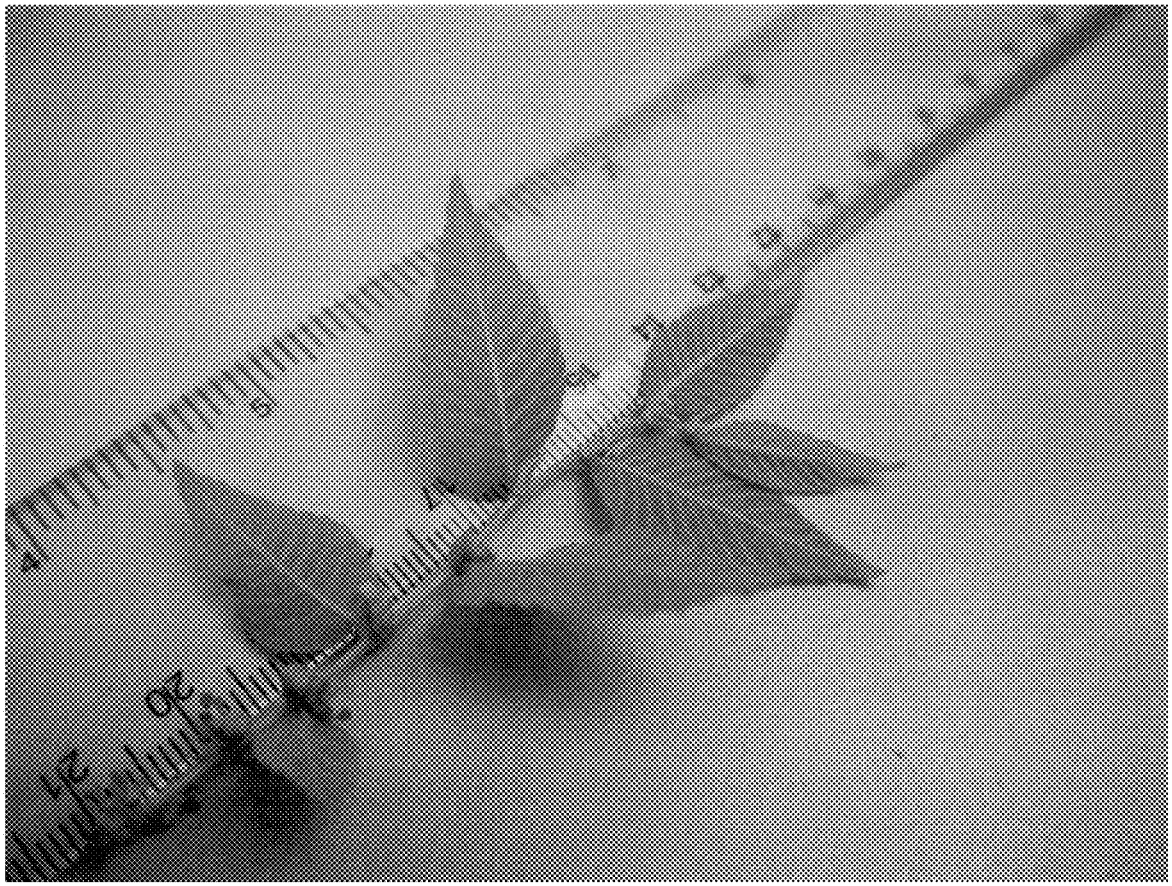
FIG. 5: Shows a close up of pistillate flowers on shoot tips with scale.
Figure 6:
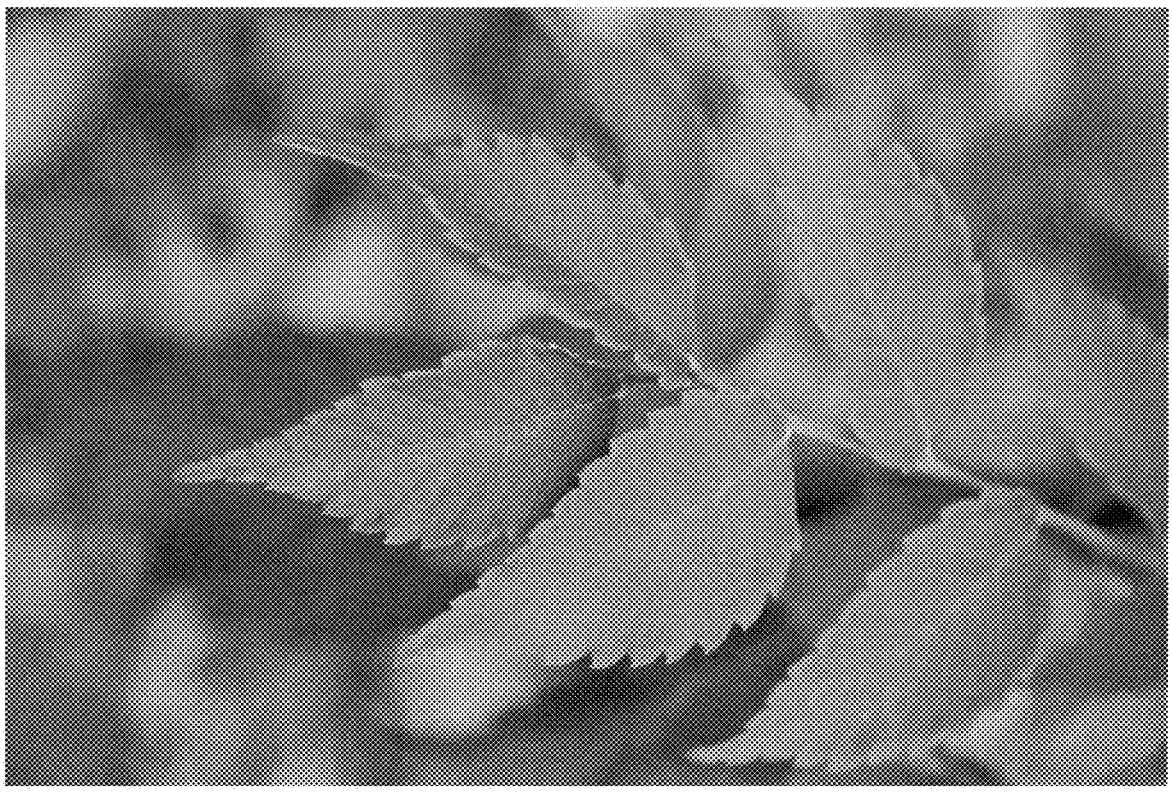
FIG. 6: Shows summer foliage on 2 year old trees.
Figure 7:
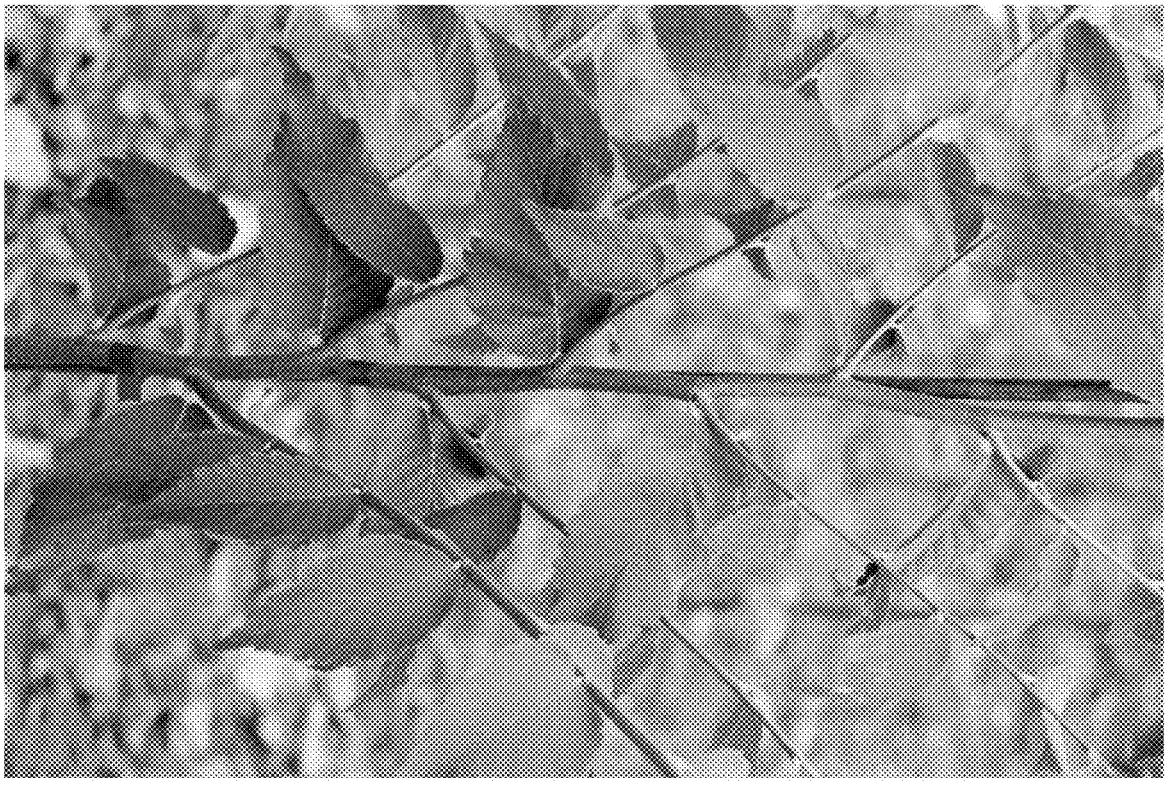
FIG. 7: Shows summer foliage & branch angles on 2 year old trees.
Figure 8:
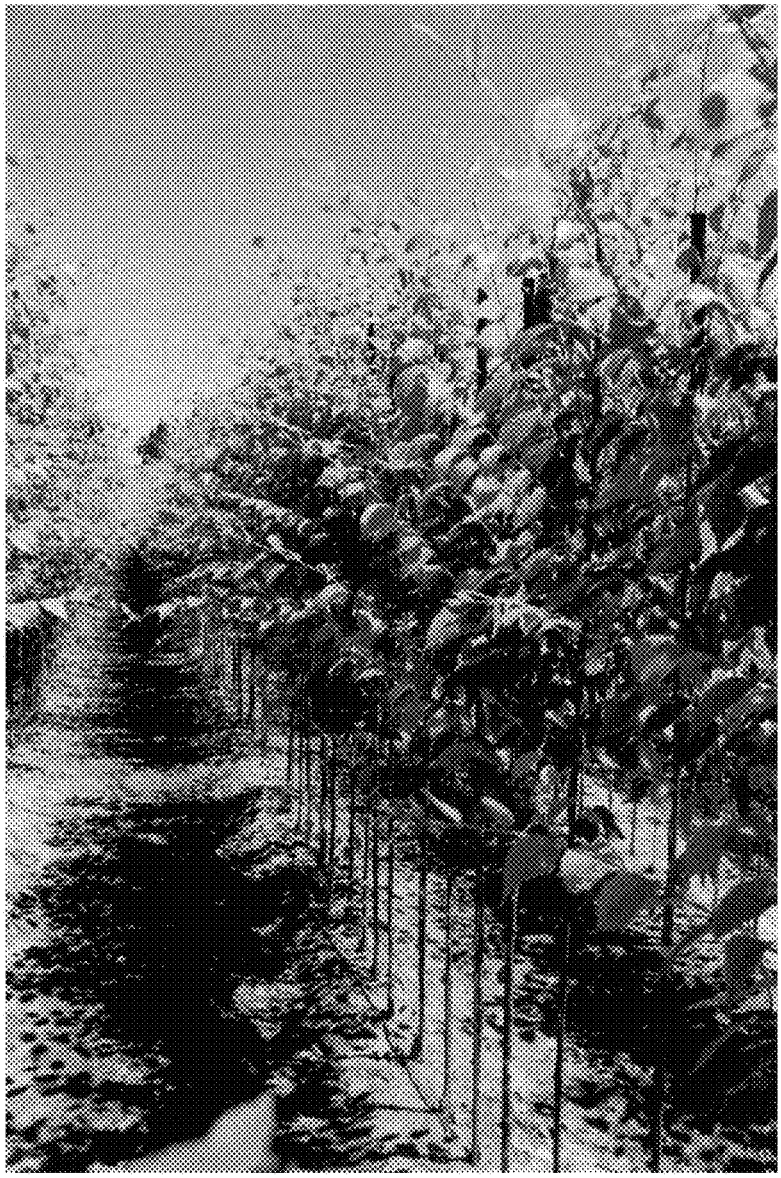
FIG. 8: Shows a nursery production row of 2 year old trees.
Figure 9:
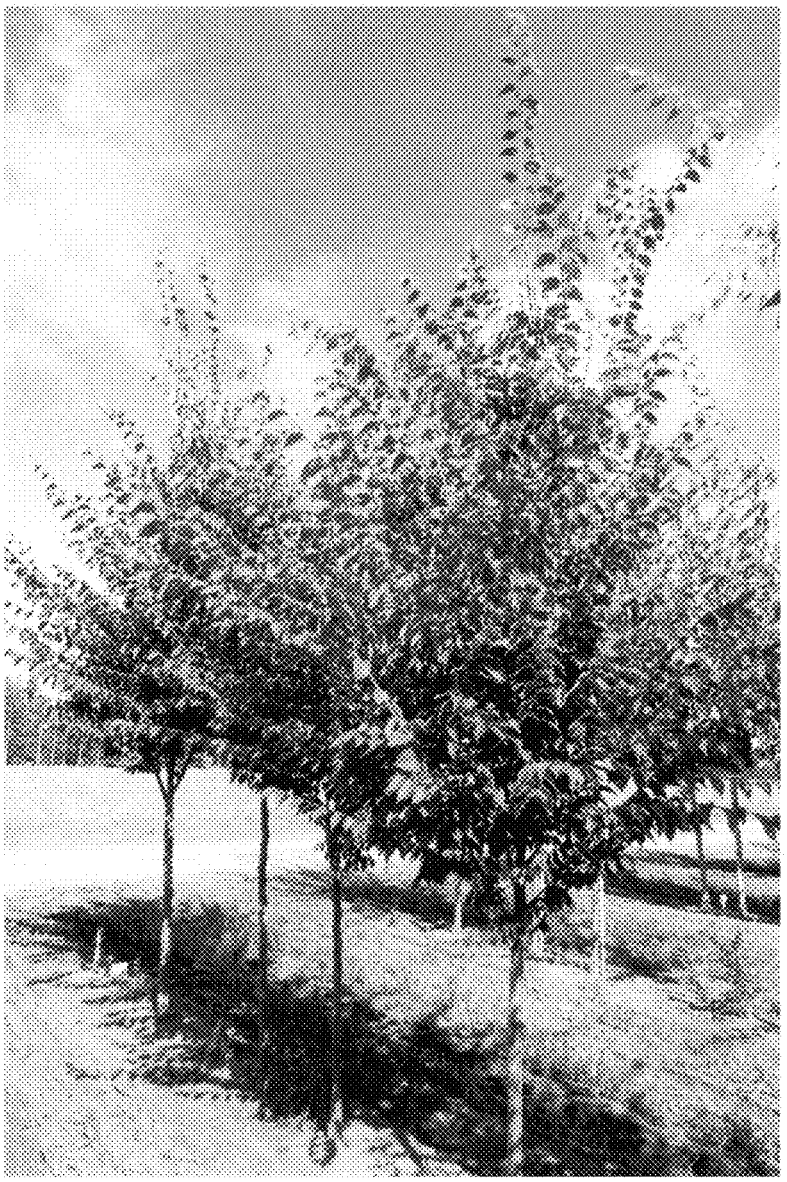
FIG. 9: Shows a nursery production row of 3 year old trees.

The following detailed description of the 'JFS KW4ZS' variety is based on observations of a 10 year old tree growing in Boring, Oreg. and of two and three year old asexually reproduced progeny. The observed progeny were trees which were growing in Boring, Oreg. & Canby, Oreg. Color descriptions are made with reference to The Royal Horticultural Society (London) Colour Chart © 1986, except where ordinary dictionary significance of color is indicated. Scientific name: *Zelkova serrata* 'JFS KW4ZS'.

Parentage:

*Seed parent*.—An unknown tree of the species *Zelkova serrata*.

*Pollen parent*.—Open pollinated by an unknown tree of the species *Zelkova serrata*.

Tree:

*Overall shape*.—Upright vase.

*Height*.—At 10 years of age, about 7.5 meters high.

*Width*.—At 10 years of age 5 meters spread.

*Caliper* (*trunk diameter*).—At 10 years of age, about 170 mm at 100 mm height, 145 mm at 1 m height.

*Trunk*.—Strong and straight.

*Trunk bark texture*.—Smooth.

*Trunk bark color*.—Greyed Green 197A.

*Immature bark color*.—Grey Brown 199B.

*Mature bark color*.—Greyed Green 197C.

*Lenticels*.—Absent in main trunk and older branches.

*Branch color*.—Greyed Brown 197C.

*Branch lenticels*.—Greyed Orange 167B, 1 mm long by 0.5 mm wide on younger branches.

*Dormant buds*.—Brown 200D, 1-2 mm long by 0.5 mm-1 mm wide: acute with overlapping scales.

*Internodes*.—Average internode length is about 35 mm-50 mm on one-year old shoots.

*Hardiness*.—Has tolerated temperatures to 10° F. in Canby, Oreg. which is the lowest temperature experienced at this location for this period. It is believed to have zone 5 cold hardiness similar to other plants of the same species.

Leaves: Except as otherwise noted, observations are from twenty vigorous growth leaves.

*Arrangement*.—Alternate.

*Type*.—Simple, entire.

*Texture*.—Smooth but directionally oriented pubescence can give the leaf a rough feel on the upper surface.

*Sheen*.—Glossy when leaves first emerge but then dull on upper surface matte on the lower surface.

*Length*.—Averaging 70 mm-110 mm.

*Width*.—Averaging 35 mm to 45 mm.

*Petioles*.—4 mm to 5 mm long, about 1 mm-2 mm in diameter, color Yellow-Green 151B.

*Overall shape*.—Long ovate.

*Margin*.—Serrate.

*Tip*.—Acuminate.

*Base*.—Subcordate.

*Spring leaf color*.—Yellow Green between 149A to 145A.

*Summer leaf color*.—Upper leaf surface: Green 137A. Lower leaf surface: Yellow Green 146B. Vein: Yellow Green 153A.

*Fall leaf color*.—Foliage turns to Greyed Orange between 168A to 172A.

*Fall color begins*.—October 25th (Boring, Oreg. 2021).

*Fall color peak*.—November 15st (Boring, Oreg. 2021).

*Fall color ends*.—November 30th (Boring, Oreg. 2021).

*Pubescence*.—Yes on the upper surface.

*Persistence*.—Tree is deciduous.

*Venation pattern*.—Pinnate.

Flowers:

*Overall*.—Monoecious, separate staminate & pistillate flowers emerge with the new leaves in the leaf axils on new shoots in the spring.

*The flowers are inconspicuous and are of no ornamental value.*

*Size*.—Staminate flowers are 4 mm-5 mm in diameter emerging in the leaf axils of the lower leaves. The pistillate flowers are solitary, sessile in the upper leaf axils and are 1 mm-1.5 mm in diameter.

*Unopened bud*.—Yellow-Green 144B-144C.

*Stamens*.—About 10 to 12 stamens, 2 mm to 4 mm.

*Anthers*.—Yellow Green 146A 0.25 mm in diameter.

*Pistil*.—Orange White 159D.

*Pollen*.—Yellow 11B.

*Flowering date*.—In Boring, Oreg. 2021 (an average bloom year). First blooms April 15th, peak bloom April 25th, last bloom May 5th.

Fruit: Observations are from a sampling of typical seeds.

*Type*.—Dried drupe, ovate, wingless.

*Size*.—Typical fruit is 3 mm to 4 mm in length by 2 mm to 3 mm wide.

*Color*.—Immature fruit is Green 143A.

*Seeds*.—Typically 1 per fruit, ovate 2 mm to 3 mm long by 1 mm to 2 mm wide.

*Seed color*.—Mature seed is Greyed Brown 199B.

Pest/disease resistance: 'JFS KW4ZS' exhibits no greater or lesser degree of pest or disease resistance or susceptibility when compared to other *Zelkova serrata* cultivars such as 'JFS-KW1' 'Green Vase', and 'Musashino'

COMPARISON TO THE SEED PARENT

Compared to a typical *Zelkova serrata* tree, 'JFS KW4ZS' develops into a more compact, smaller tree with a symmetrical, more upright branch structure.

TABLE 1

COMPARISON TO OTHER SIMILAR VARIETIES:

| | *Zelkova serrata* 'JFS KW4ZS' | *Zelkova serrata* 'JFS-KW1' U.S. Plant Pat. No. 20,996 | *Zelkova serrata* 'Green Vase' U.S. Plant Pat. No. 5,080 |
|---|---|---|---|
| Relative size at 10 years Old | Height 7.5 m Spread 5.0 m | Height 3.5 m Spread 2.7 m | Height 10 m Spread 6.5 m |
| Form | Compact upright vase | Compact oval to vase | Vase shaped, arching upright branches |

TABLE 1-continued

| COMPARISON TO OTHER SIMILAR VARIETIES: | | | |
|---|---|---|---|
| | *Zelkova serrata* 'JFS KW4ZS' | *Zelkova serrata* 'JFS-KW1' U.S. Plant Pat. No. 20,996 | *Zelkova serrata* 'Green Vase' U.S. Plant Pat. No. 5,080 |
| Summer Upper Leaf Color | Green 137A | Green 139A | Green 136A |
| Summer Lower Leaf Color | Yellow-Green 146B | Yellow-Green 147A-147B | Yellow-Green 144A |
| Leaf Petiole length | 4 mm to 5 mm | 3 mm | 4 mm to 6 mm |
| Typical Internode Length | 35 mm to 50 mm | 12 mm to 29 mm | 45 mm-60 mm |
| Fall Color | Greyed-Orange between 168A to 172A | Yellow 11A to Yellow-orange 22A. | Greyed-Orange 170A |

TABLE 1-continued

| COMPARISON TO OTHER SIMILAR VARIETIES: | | | |
|---|---|---|---|
| | *Zelkova serrata* 'JFS KW4ZS' | *Zelkova serrata* 'JFS-KW1' U.S. Plant Pat. No. 20,996 | *Zelkova serrata* 'Green Vase' U.S. Plant Pat. No. 5,080 |
| Branching | Upright, then moderately vase shaped, sturdy, symmetrical | Dense, stiff, more spreading, finely branched | Long, slender, lax and arching |
| Branch angles on the main stem on 2 YR old trees | 30 to 35 degrees | 45 to 50 degrees | 35 to 40 degrees |

I claim:

1. A new and distinct variety of *Zelkova* tree named 'JFS KW4ZS', substantially as illustrated and described herein.

* * * * *